United States Patent
Barbut

(10) Patent No.: US 6,817,985 B2
(45) Date of Patent: Nov. 16, 2004

(54) INTRAVASCULAR SPINAL PERFUSION AND COOLING FOR USE DURING AORTIC SURGERY

(75) Inventor: Denise R. Barbut, New York, NY (US)

(73) Assignee: CoAxia, Inc., Maple Grove, MN (US)

( * ) Notice: Subject to any disclaimer, the term of this patent is extended or adjusted under 35 U.S.C. 154(b) by 239 days.

(21) Appl. No.: 10/045,421

(22) Filed: Jan. 11, 2002

(65) Prior Publication Data

US 2002/0058900 A1 May 16, 2002

Related U.S. Application Data

(63) Continuation of application No. 09/282,771, filed on Mar. 31, 1999, now Pat. No. 6,355,010.

(51) Int. Cl.[7] .......................... A61M 37/00; A61M 5/00; A61F 7/12
(52) U.S. Cl. .......................... 604/6.13; 604/8; 604/6.16; 604/113; 128/898
(58) Field of Search .............................. 604/4.01, 5.01, 604/6.01, 6.13, 6.11, 8–10, 258, 6.14, 113–114, 523, 284, 500, 506–507; 128/898; 137/833–834, 836–837, 839, 118.01; 251/142, 149, 149.2; 623/1.1, 1.11, 1.15, 1.16, 3.1, 3.26, 328

(56) References Cited

U.S. PATENT DOCUMENTS

| | | | | |
|---|---|---|---|---|
| 3,435,824 A | * | 4/1969 | Gamponia | 604/8 |
| 3,516,408 A | * | 6/1970 | Montanti | 604/8 |
| 4,398,907 A | * | 8/1983 | Crais | 604/8 |
| 4,712,551 A | * | 12/1987 | Rayhanabad | 604/8 |
| 4,979,937 A | | 12/1990 | Khorasani | |
| 5,288,290 A | | 2/1994 | Brody | |
| 5,391,142 A | * | 2/1995 | Sites et al. | 604/6.13 |
| 5,746,709 A | | 5/1998 | Rom et al. | |
| 5,957,963 A | | 9/1999 | Dobak, III | |
| 6,436,087 B1 | * | 8/2002 | Lewis et al. | 604/508 |
| 6,530,894 B1 | * | 3/2003 | Barbut | 604/9 |
| 6,555,057 B1 | * | 4/2003 | Barbut et al. | 422/44 |

* cited by examiner

Primary Examiner—Patricia M. Bianco
(74) Attorney, Agent, or Firm—O'Melveny & Myers LLP

(57) ABSTRACT

Cooled and oxygenated blood is shunted from the proximal aorta into the open ends of intercostal arteries severed during thoracoabdominal aortic surgery to prevent or minimize the effects of spinal ischemia. This cooled perfusion can be accomplished with a variety of perfusion assemblies. For instance, a single vessel perfusion assembly can be employed to shunt the oxygenated blood from the aorta to the lumen of a single intercostal artery. Cooled perfusion can also be performed with a branched multiple vessel perfusion assembly, which includes a branched conduit comprising a common portion and branch portions. In operation, oxygenated blood flows from the aorta into the inflow cannula, through the blood flow conduit, out of the one or more outflow cannula, and into the intercostal arteries.

29 Claims, 10 Drawing Sheets

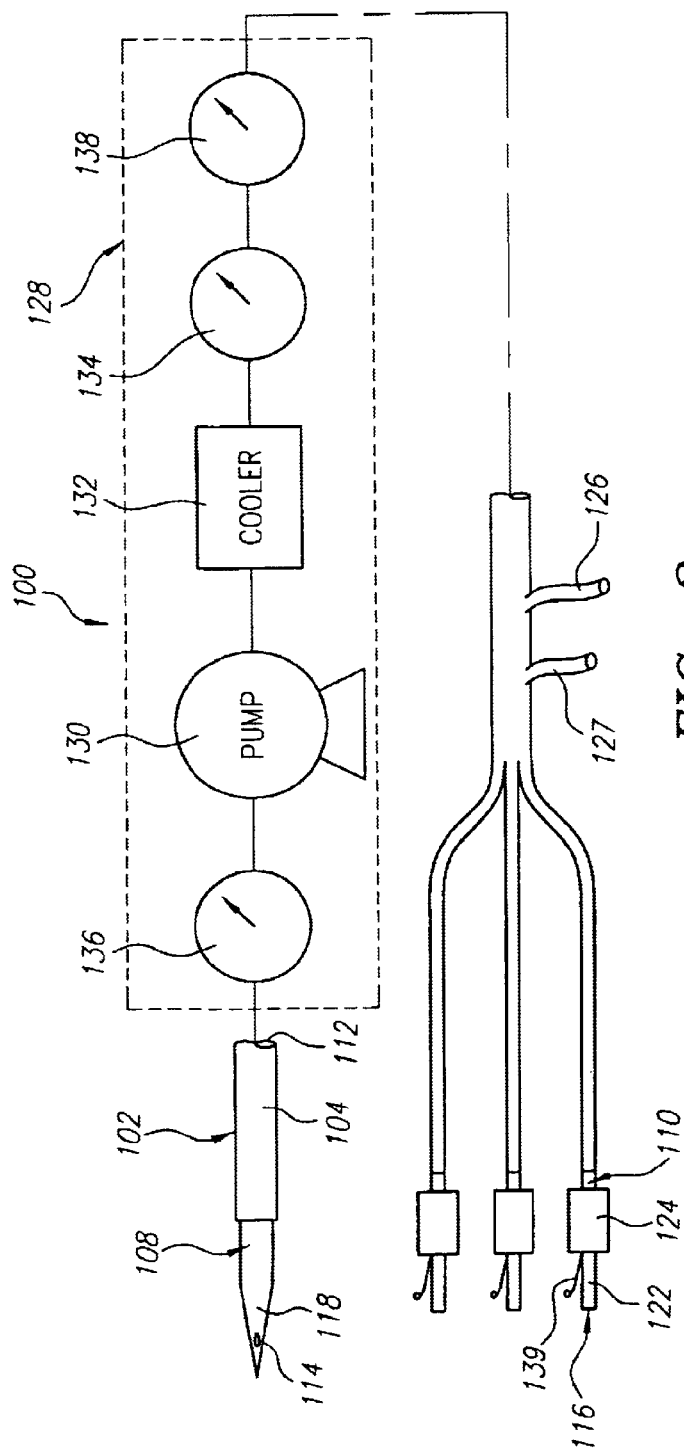
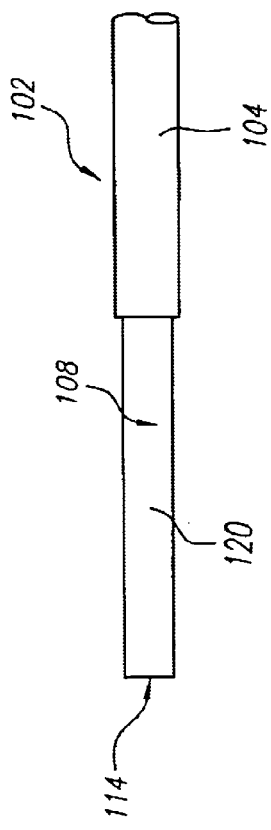
FIG. 2
FIG. 3

INTRAVASCULAR SPINAL PERFUSION AND COOLING FOR USE DURING AORTIC SURGERY

This is a continuation of U.S. application Ser. No. 09/282,771, filed Mar. 31, 1999, now U.S. Pat. No. 6,355,010, incorporated herein by reference in its entirety.

FIELD OF THE INVENTION

The present invention relates generally to medical methods and devices, and more particularly, to methods and devices for cooling and perfusing the spinal vasculature of a patient during thoracoabdominal aortic surgery.

BACKGROUND

Approximately 50,000 patients undergo surgical procedures on the aorta each year for the treatment of various conditions, such as aortic aneurysms, occlusional diseases and aortic dissection. An exemplary procedure includes conventional aortic grafting, which involves clamping the aorta upstream from the damaged region to prevent blood loss at the surgical site, excising a cylindrical portion of the aorta encompassing the damaged region, and replacing the removed portion of the aorta with a graft. During this procedure, the intercostal arteries leading to the damaged region of the aorta are individually severed from the aorta.

The cessation of blood flow through the aorta causes spinal ischemia in about 10–15% of patients, due to the reduction or cessation of oxygenated blood within the spinal vasculature that would normally be supplied thereto by the intercostal arteries downstream from the clamped portion of the aorta. Because spinal ischemia can quickly lead to irreversible spinal tissue damage, a minimal amount of time is allowed to suture the intercostal arteries onto the graft. Often, when the intercostal arteries are severed from the aorta, none or very few of them are sutured onto the graft due to the time limitations. The aortic clamp is removed after the graft is attached, thereby supplying oxygenated blood to the spinal vasculature via the unsevered intercostal arteries, albeit in a non-robust manner. Spinal neurological damage is directly related to cross-clamp time and the number of severed intercostal arteries.

To ease reattachment to the graft, the intercostal arteries are sometimes integrally severed from the aorta, i.e., patches of the posterior wall of the aorta are excised, each of which carries several intercostal arteries. After the aorta has been grafted, the aortic patch can be sutured onto the graft, minimizing the amount of time it takes to connect the intercostal arteries to the aorta. Regardless of whether the intercostal arteries are individually or integrally severed from the aorta, however, there remains danger of causing irreversible damage to the spinal tissue resulting from ischemia.

For these reasons, it would be desirable to provide improved methods and assemblies for preventing spinal ischemia during the performance of surgical procedures on the aorta, and allowing more time to restore a robust blood flow within the spinal vasculature.

SUMMARY OF THE INVENTION

The invention provides single or multiple vessel perfusion assemblies and methods for selectively treating the spinal vasculature of a patient during thoracoabdominal surgery.

Methods performed in accordance with the present invention comprise perfusing the spinal vasculature with a medium by flowing a medium into the open ends of one or more intercostal arteries. The intercostal arteries can be accessed by individually or integrally severing the intercostal arteries from the aorta, or alternatively, the intercostal arteries can be accessed through a puncture or slit within the wall of the aorta. Preferably the medium is cooled to induce hypothermia within the spinal vasculature without cooling the rest of the body (selective spinal hypothermia). The cooled medium can be composed of a biocompatible liquid, such as, e.g., a saline solution, that is flowed from an external source and is cooled. Alternatively, the cooled medium can be composed of oxygenated blood that is shunted from a oxygenated blood filled cavity, such as the heart or proximal aorta upstream from the intercostal arteries and cooled. The characteristics of the cooled medium, such as, e.g., the temperature, flow rate and pressure of the medium is preferably controlled to maintain a viable environment for the spinal vasculature. The methods of the present invention can be performed by employing any vessel perfusion assembly, but are preferably performed by flowing a medium into the plurality of intercostal arteries, which can be facilitated by employing single and multiple vessel perfusion assemblies, such as those described herein.

Multiple vessel perfusion assemblies constructed in accordance with the present invention provide a means for simultaneously flowing a medium into the open ends of a plurality of vessels. In a first embodiment, the multiple vessel perfusion assembly includes a branched conduit having a common portion, an inflow cannula formed at one end of the common portion and a plurality of outflow cannulae respectively formed at the other end of the common portion. The branched conduit includes a lumen for conveyance of a medium therethrough. The inflow cannula can comprise any tubular member configured to be inserted through the wall of the heart or proximal aorta, and the outflow cannulae can comprise any tubular members configured to be inserted into the open ends of vessels. The inflow cannula includes an inlet, and the outflow cannulae include outlets, which are in fluid communication with the lumen of the branched conduit. In this manner, insertion of the inflow cannula through the heart or aortic wall and respective insertion of the plurality of outflow cannulae into the open ends of the vessels provides flow of oxygenated blood from the heart or aorta into the vessels. The branched multiple vessel perfusion assembly further includes a cooler for cooling the medium as it passes through the lumen of the branched conduit. The cooler may be disposed within the lumen of the inflow cannulae.

In a second embodiment, the multiple vessel perfusion assembly includes a conduit, an inflow cannula formed at one end of the conduit, and a perfusion chamber formed at the other end of the conduit. The conduit includes a lumen, and the inflow cannula and perfusion chamber respectively include an inlet and a substantially enclosed cavity, which are in fluid communication with the lumen of the conduit. The perfusion chamber includes vessel engaging outlets, which are configured to securely receive the open ends of a plurality of integrally severed vessels (an aortic patch). In this manner, insertion of the inflow cannula through the heart or proximal aortic wall, and disposition of the open ends of the severed vessels into the vessel engaging outlets provides simultaneous flow of oxygenated blood from the heart or aorta into the vessel inlets contained within the aortic patch.

A single vessel perfusion assembly constructed in accordance with the present invention provides a means for flowing a medium into the open end of a vessel. In an embodiment, the single vessel perfusion assembly includes a conduit, an inflow cannula formed at one end of the conduit and an outflow cannula formed at the other end of the conduit. The conduit includes a lumen for conveyance of a medium therethrough. The inflow cannula includes an inlet, and the outflow cannula includes an outlet, which are in fluid communication with the lumen of the conduit. In this manner, insertion of the inflow cannula through the heart or aortic wall and insertion of the outflow cannula into the open end of the vessel provides flow of oxygenated blood from the heart or aorta into the vessel.

Alternatively, the above multiple vessel perfusion assemblies can forego the employment of an inflow cannula. In this case, a medium, such as, e.g., a saline solution, can be suitably introduced into the conduit of the multiple vessel perfusion assemblies. Preferably, the multiple vessel perfusion assemblies further include control devices for conditioning the medium to maintain a viable environment for the tissue to which the vessels lead. For instance, a cooler and associated thermostat can be used to cool and control the temperature of the medium. A pump and associated manometers can be used to control the flow rate and pressure of the medium.

Other and further objects, features, aspects, and advantages of the present invention will become better understood with the following detailed description of the accompanying drawings.

BRIEF DESCRIPTION OF THE DRAWINGS

The drawings illustrate both the design and utility of preferred embodiments of the present invention, in which:

FIG. 2 illustrates a first preferred embodiment of a multiple vessel perfusion assembly constructed in accordance with the present invention;

FIG. 3 illustrates an alternative embodiment of the inflow cannula employed in the multiple vessel perfusion assembly of FIG. 2;

DETAILED DESCRIPTION OF THE PREFERRED EMBODIMENTS

Figure 1:
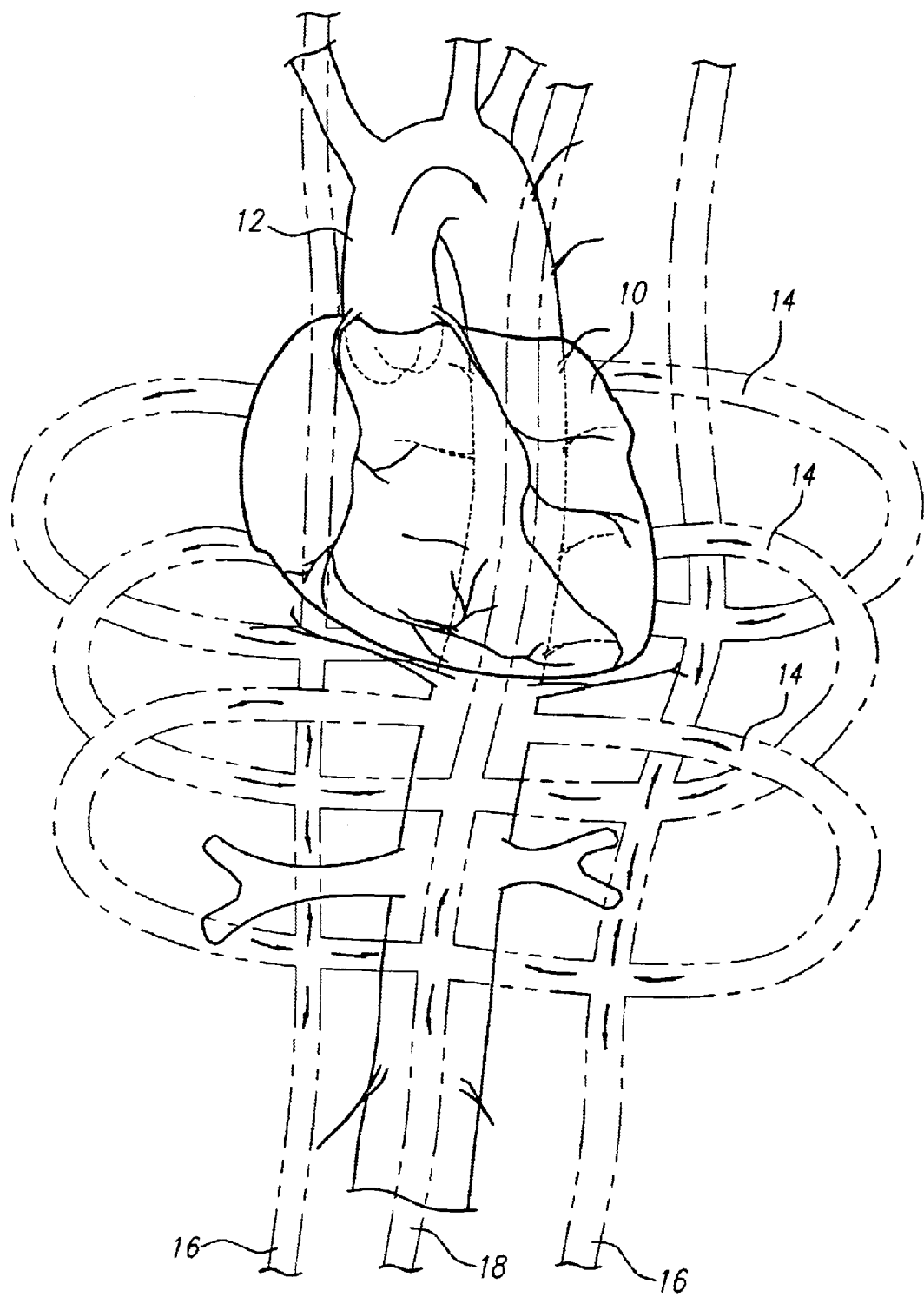
FIG. 1 illustrates the systemic arterial circulation of a patient relevant to the present invention.

Referring to FIG. 1, arterial circulation relevant to the methods of the present invention will be briefly described. Oxygenated blood (represented by arrows) from the heart 10 normally flows through the aorta 12 and into a multitude of intercostal arteries 14, which branch off of the aorta 12. The oxygenated blood then flows from the intercostal arteries 14 into the spinal vasculature, i.e., the posterior spinal arteries 16 and the anterior spinal artery 18 (shown partially in phantom), where it is distributed to the spinal tissue. Because the spinal vasculature is common to all of the intercostal arteries 14, oxygenated blood can still be distributed to the entire spinal tissue even if the blood flow within some of the intercostal arteries 14 ceases. Spinal ischemia will result, however, if the number of intercostal arteries 14 through which the blood flow is ceased is too great, which often occurs as a result of thoracoabdominal aortic surgery.

Referring to FIG. 2, a branched multiple vessel perfusion assembly 100 constructed in accordance with a preferred embodiment of the present invention is described. The branched multiple vessel perfusion assembly 100 can be used to shunt blood from the aorta 12 to a plurality of severed arteries, such as, e.g., severed intercostal arteries 14. The vessel perfusion assembly 100 generally includes a branched conduit 102 having a common portion 104, an inflow cannula 108 formed at one end of the common portion 104, and a plurality of outflow cannulae 110 respectively formed at the other end of the common portion 104. The inflow cannula 108 is configured to be inserted through the wall of the aorta 12, and each of the outflow cannulae 110 are configured to be inserted into the open end of a severed intercostal artery 14. The branched conduit 102 includes a blood lumen 112 extending therethrough. The inflow cannula 108 includes an inlet 114, and the each of the outflow cannulae 110 includes an outlet 116. The inlet 114 and outlets 116 are in fluid communication with the blood lumen 112, such that blood entering the inlet 114 flows through the blood lumen 112 and exits the outlets 116.

In the illustrated embodiment, the branched conduit 102 is formed of elastomeric tubing. The inflow cannula 108 includes a hollow needle 118 having a sharpened distal tip, such that the inflow cannula 108 can penetrate the wall of the aorta 12. The inlet 114 is located on the hollow needle 118. Alternatively, as shown in FIG. 3, the inflow cannula 108 includes a blunt access tube 120, which can be inserted inside the aorta 12 through a small incision or puncture previously made in the wall of the aorta 12. Each of the outflow cannulae 110 is preferably composed of a rigid tapered body 122 to facilitate insertion thereof within the open end of the severed intercostal artery 14.

Each of the outflow cannulae 110 includes a balloon occluder 124 located proximal to the outlets 116 to prevent leakage of the blood from the open end of the severed intercostal artery 14 when the outflow cannula 110 is disposed therein and blood is flowed out the outlet 116. The elongate tubing 102 includes an inflation port 126, which is in fluid communication with the cavities of the respective balloon occluders 124 via an inflation lumen (not shown).

Conveyance of inflation medium into and out of the inflation port 126 effects alternate inflation and deflation of the balloon occluders 124. In this manner, each of the balloon occluders 124 can be deflated to facilitate the insertion and removal of the respective outflow cannula 110 into and out of the open end of the severed intercostal artery 14, and inflated to sealingly secure the respective outflow cannula 110 within the open end of the severed intercostal artery 14. In alternative embodiments, the inflation port 126 is in fluid communication with the plurality of balloon occluders 124 via a plurality of respective inflation lumens (not shown). The branched multiple vessel perfusion assembly 100 further includes a drug deliver port 127 to allow a physician to introduce drugs, such as, e.g., a neuroprotective agent, into the oxygenated blood.

The branched multiple vessel perfusion assembly 100 includes a control mechanism 128 placed within the path of the common portion 104 of the branched conduit 102. The control mechanism comprises a pump 130, typically a peristaltic pump, and a cooler 132. Operation of the pump 130 facilitates and controls the flow of blood through the branched conduit 102, while operation of the cooler 132 cools the blood, thereby cooling and further protecting the spinal tissue. The control mechanism 128 further includes a thermostat 134 downstream from the cooler 132, thereby ensuring that the desired temperature of the cooled blood is achieved. The branched multiple vessel perfusion assembly 100 also further include manometers 136 and 138 respectively downstream and upstream from the pump 130, thereby ensuring that the desired blood pressure within the aorta 12 and the severed intercostal arteries 14 is achieved. The thermostat 134 and manometers 136 and 138 directly provide feedback to the cooler 132 and pump 130, thereby facilitating automatic control of the blood temperature and respective blood pressures within the aorta 12 and severed intercostal arteries 14. Preferably, the blood pressure within the intercostal arteries 14 are maintained above 60 mm, at least for normalthermia. Alternatively, the physician can read the thermostat 134 and manometers 136 and 138, allowing the physician to manually control the pump 130 and cooler 132. Alternatively, a manometer 139 can be located on each outflow cannula 116 to provide a direct measurement of the blood pressure in each of the severed intercostal arteries 14.

As will be described in further detail below, insertion of the inflow cannula 108 into the aorta upstream from the severed intercostal arteries 14, insertion of the outflow cannulae 116 into the respective severed intercostal arteries 14, and subsequent operation of the inflation device and control mechanism 128 provides a controlled flow of cooled and oxygenated blood into the spinal arteries 16 via the severed intercostal arteries 14.

In alternative embodiments, employment of the inflow cannula 108 can be foregone, in which case, a medium such as, e.g., saline solution, can be flowed from an exterior source into the common portion 104 of the branched conduit 112.

It should be noted that although the branched multiple vessel perfusion assembly 100 has particular applications in the perfusion of oxygenated blood from the aorta 12 into the open ends of severed intercostal arteries 14, it can also be employed in other applications requiring the perfusion of oxygenated blood from any large artery to a plurality of open ended vessels without straying from the principles taught by this invention.

Figure 4:
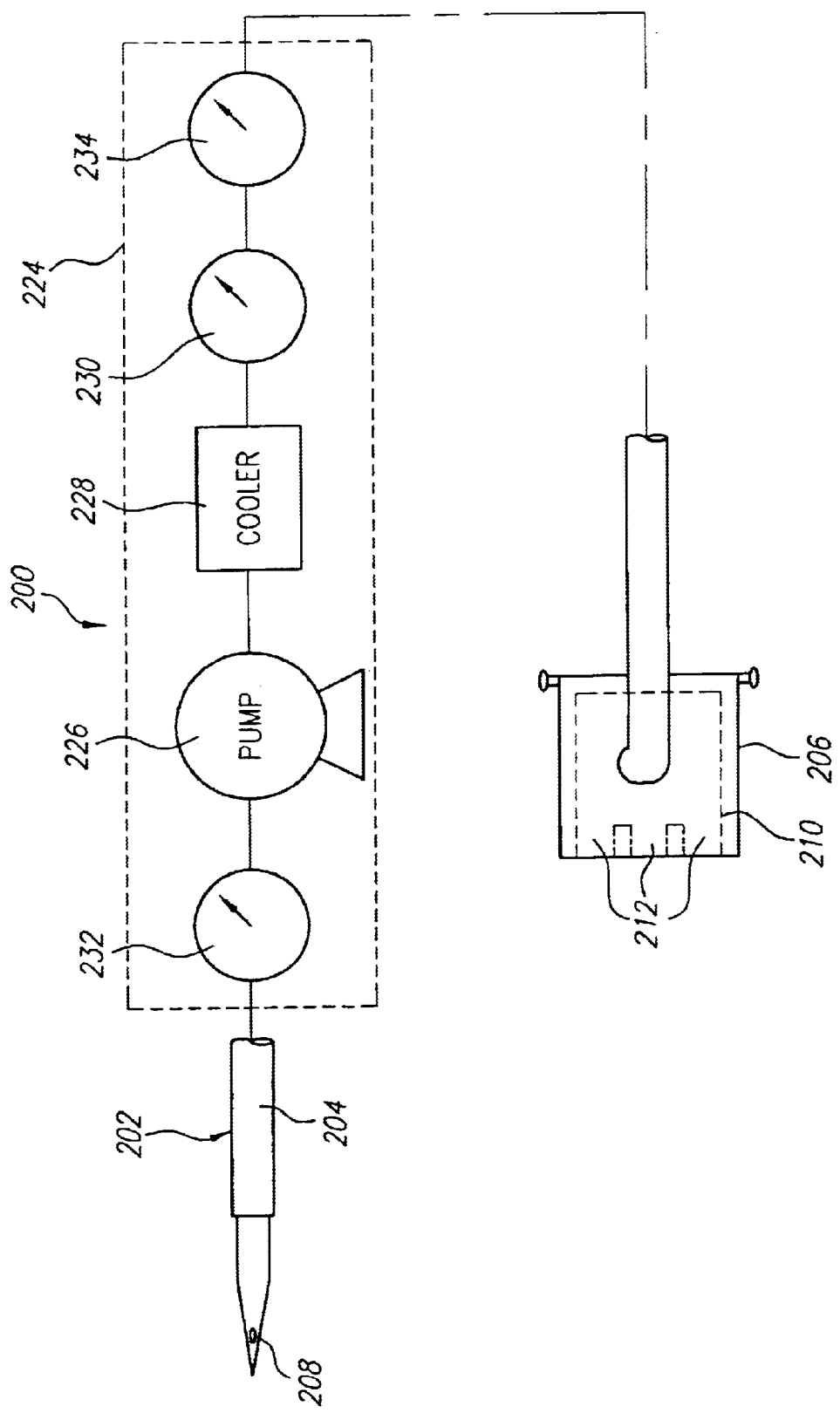
FIG. 4 illustrates a second preferred embodiment of a multiple vessel perfusion assembly constructed in accordance with the present invention.

Referring to FIG. 4, a chambered multiple vessel perfusion assembly 100 constructed in accordance with a preferred embodiment of the present invention is described. Like the branched multiple vessel perfusion assembly 100, the chambered multiple vessel perfusion assembly 100 can be used to shunt blood from the aorta 12 to the open ends of severed intercostal arteries 14. The chambered multiple vessel perfusion assembly 100 generally includes a blood flow conduit 202, an inflow cannula 204 formed at one end of the blood flow conduit 202, and a perfusion chamber 206 formed at the other end of the blood flow conduit 202. The inflow cannula 204 includes a blood flow inlet 208, and the perfusion chamber 206 includes a substantially enclosed cavity 210 (shown in phantom), such that blood entering the blood flow inlet 208 flows through the blood flow conduit 202 and into the cavity 210. The perfusion chamber 206 includes a plurality of vessel engaging outlets 212 (shown in phantom) configured to receive the open ends of intercostal arteries 14 to place the lumens of the intercostal arteries 14 in fluid communication with the substantially enclosed cavity 210.

Figure 5:
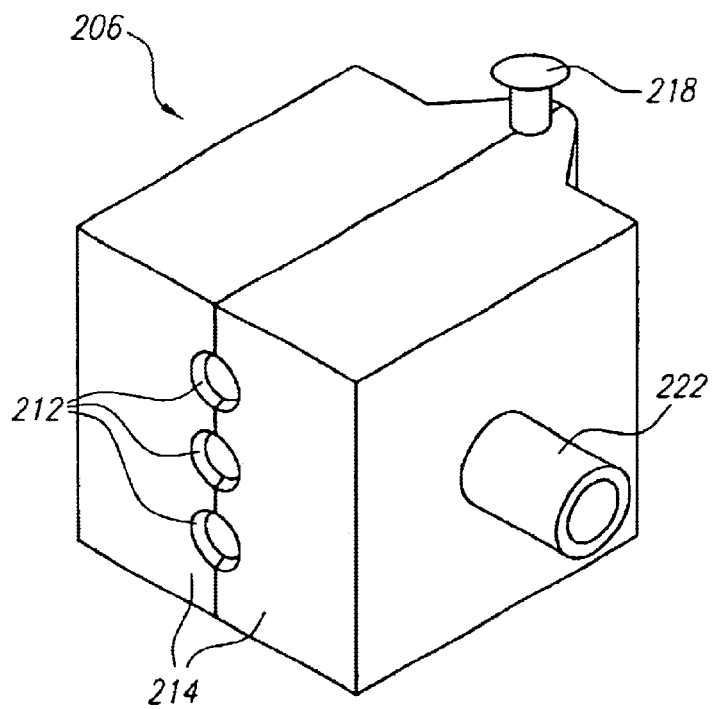
FIG. 5 illustrates a perfusion chamber employed in the multiple vessel perfusion assembly of FIG. 4, which is particularly shown in a closed position.
Figure 6:
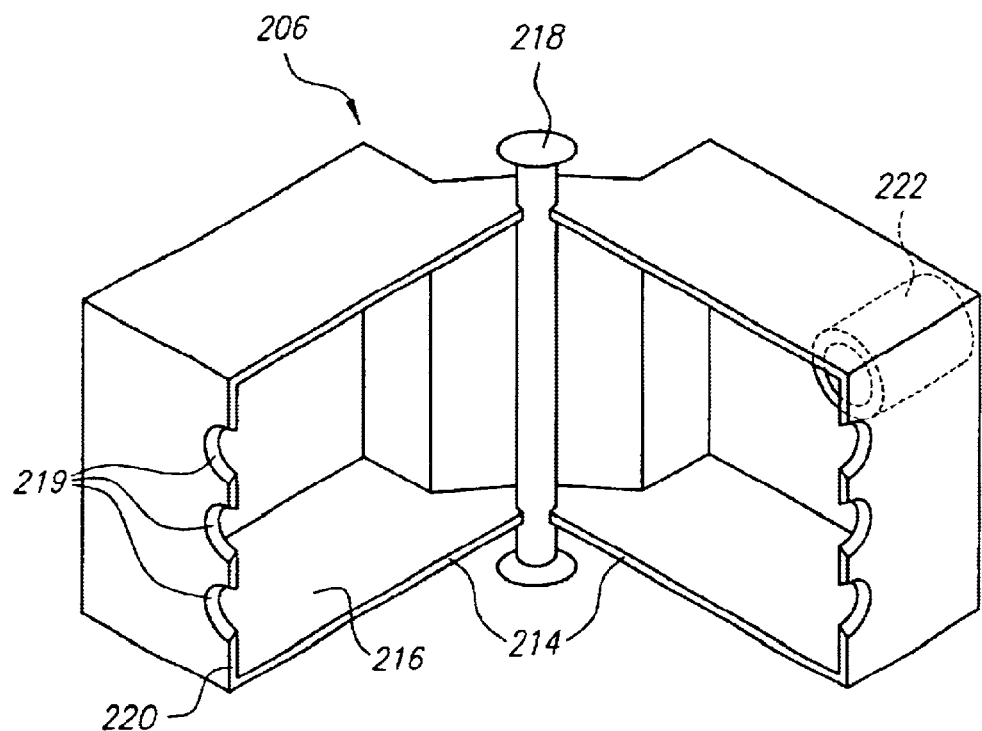
FIG. 6 illustrates a perfusion chamber employed in the multiple vessel perfusion assembly of FIG. 4, which is particularly shown in an open position.

In the illustrated embodiment, the blood flow conduit 202 is formed of elastomeric tubing. The inflow cannula 204 is constructed in a manner similar to the inflow cannula 108 described above. Referring to FIGS. 5 and 6, the perfusion chamber 206 includes a pair of opposing structures 214, each having an open cavity 216. The perfusion chamber 206 further includes a hinge 218 on which the opposing structures 214 are mounted, such that the perfusion chamber 206 can be alternately placed into a closed position (FIG. 5) and an open position (FIG. 6). Each of the opposing structures 214 includes a plurality of matching notches 219 formed on an edge 220 opposite the hinge 218. One of the opposing structures 214 includes an inlet port 222, which is in communication with the substantially enclosed cavity 210 and is configured to be coupled to the end of the conduit 202.

In this manner, the open cavities 216 and matching notches 219 of the opposing structures 214 respectively form the cavity 210 and plurality of vessel engaging outlets 212 when the perfusion chamber 206 is in the closed position. The vessel engaging outlets 212 are sized to sealingly engage the open ends of the intercostal arteries 14, such that blood enters the lumens of the intercostal arteries 14 when the open ends of the intercostal arteries 14 are disposed within the vessel engaging outlets 212. The spacing between the vessel engaging outlets 212 are preferably equal to the spacing between the integrated plurality of intercostal arteries 14 to facilitate the engagement thereof.

Like the branched multiple vessel perfusion assembly 100 described above, the chambered multiple vessel perfusion assembly 100 includes a control mechanism 224, which includes a pump 226, cooler 228, thermostat 230 and manometers 232 and 234, placed within the path of the conduit 202.

Figure 12:
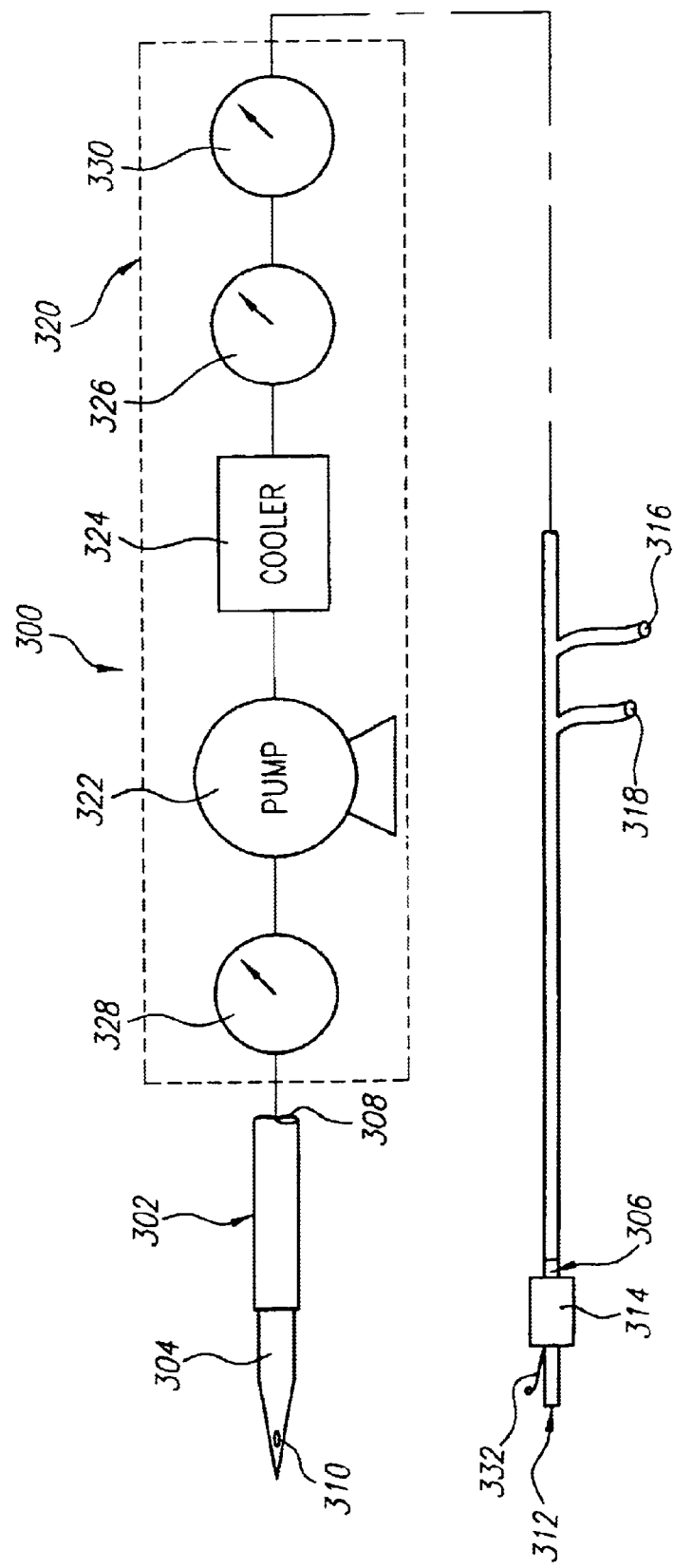
FIG. 12 illustrates a preferred embodiment of a single vessel perfusion assembly constructed in accordance with the present invention.

Referring to FIG. 12, a single vessel perfusion assembly 300 constructed in accordance with a preferred embodiment of the present invention is described. The single vessel perfusion assembly 300 can be used to shunt blood from the aorta 12 to the open end of a severed intercostal artery 14. The single vessel perfusion assembly 300 generally includes a conduit 302, an inflow cannula 304 formed at one end of the conduit 302, and an outflow cannula 306 at the other end of the conduit 302. The conduit 302 includes a blood lumen 308 extending therethrough. The inflow cannula 304 includes an inlet 310, and the outflow cannula 306 includes an outlet 312. The inlet 310 and outlet 312 are in fluid communication with the blood lumen 308, such that blood entering the inlet 310 flows through the blood lumen 308 and exits the outlet 312.

In the illustrated embodiment, the conduit 302 is formed of elastomeric tubing. The inflow cannula 304 and outflow cannula 306 are constructed similarly to the respective inflow cannula 108 and outflow cannulae 110 described above. The outflow cannula 306 includes a balloon occluder 314, and the conduit 302 includes an inflation port 316, which is in fluid communication with the cavities of the balloon occluders 314 via an inflation lumen (not shown). The single vessel perfusion assembly 300 further includes a drug deliver port 318 to allow a physician to introduce drugs, such as, e.g., a neuroprotective agent, into the oxygenated blood. Like the branched multiple vessel perfusion assembly 100 described above, the single vessel perfusion assembly 300 includes a control mechanism 320, which includes a pump 322, cooler 324, thermostat 326 and manometers 328 and 330, placed within the path of the conduit 302. Alternatively, a manometer 332 can be placed at the distal end of the outflow cannula 306, much like the manometers 139 described above.

Figure 7:
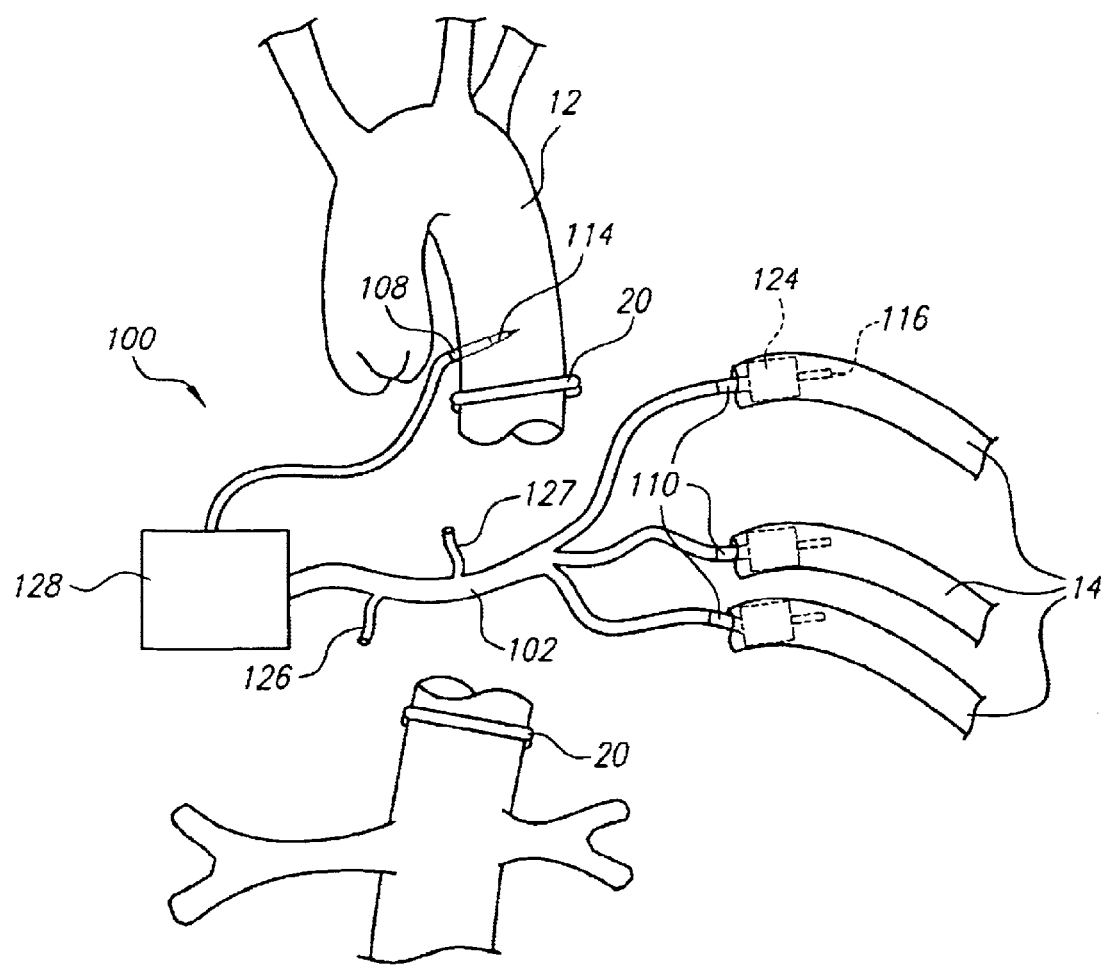
FIG. 7 illustrates a preferred method of simultaneously flowing oxygenated blood from the aorta into the open ends of a plurality of individually severed intercostal arteries by employing multiple vessel perfusion assembly of FIG. 2.

With reference to FIG. 7, selective spinal vasculature perfusion performed in accordance with a preferred method of the present invention is described in the context of an aortic grafting procedure performed on a patient. The aortic grafting procedure involves occluding the blood flow within the aorta 12 upstream and downstream from the damaged region, by suitable means, such as, e.g., a clamp 20. The intercostal arteries 14 leading to the damaged region of the aorta 12 are then individually severed from the aorta 12. The aorta 12 is then accessed at a location upstream from the occlusion, and then oxygenated blood is flowed from the aortic access location into the open ends of the individually severed intercostal arteries 14.

Perfusion of the individually severed intercostal arteries 14 can be particularly performed by employing the branched multiple vessel perfusion assembly 100 described above. The plurality of outflow cannulae 110 (shown partially in phantom) are respectively inserted within the open ends of the individually severed intercostal arteries 14, such that the balloon occluders 124 reside in the lumens thereof. Alternatively, only one of the outflow cannulae 110 is inserted into an open end of one of the individually severed intercostal arteries 14, preferably, the dominant one, i.e., the intercostal artery 14 with the most backbleeding. The inflow cannula 108 (shown partially in phantom) is inserted through the wall of the aorta 12 upstream from the clamp 20 until the blood flow inlet 114 resides within the lumen of the aorta 12. This can be accomplished either by a direct stick or through a previously made puncture or opening within the aortic wall. Inflation medium is then conveyed through the inflation port 126 to inflate the balloon occluders 124, thereby sealing the blood flow outlets 116 within the respective intercostal arteries 14. To further protect the spinal vasculature, a neuroprotective agent can be flowed into the drug delivery port 127 located on the branched conduit 102.

The control device 128 is then operated to control the perfusion of oxygenated blood within the spinal vasculature. That is, the pump 130 controllingly flows oxygenated blood from the aorta 12 into the inflow cannula 108, through the branched conduit 102, out the blood flow outlets 116, and out through the lumens of the individually severed intercostal arteries 14 to the spinal vasculature. The cooler 132 refrigerates the blood as it travels through the branched conduit 102, thereby oxygenating and cooling the spinal vasculature of the patient. Preferably, perfusion of vessels with the cooled and oxygenated blood is limited to the severed intercostal arteries 14 to further facilitate selective hypothermia within the spinal vasculature.

A preferred hypothermic temperature will be in the range from 4° C. to 35° C., more preferably from 10° C. to 20° C. The actual temperature which is maintained will depend on the temperature and flow rate of the oxygenated blood, with higher flow rates generally requiring less cooling to achieve the target temperature. Useful flow rates for the oxygenated blood will be in the range from 5 ml/minute to 1000 ml/minute, typically from 50 ml/minute to 400 ml/minute at normalthermia, and from 100 ml/minute to 200 ml/minute at hypothermia. It will be appreciated, of course, that the values of temperature and flow rate will be quite interdependent in that particular optimum values might be selected for individual patients. The temperature of the oxygenated blood and the blood pressure with the aorta 12 and intercostal arteries 14, and thus the blood flow rate, can be controlled via the thermostat 134 and manometers 136 and 138. It should be noted that blood can be flowed through fewer than all of the individually severed intercostal arteries 14, in which case, such remaining individually severed intercostal arteries 14 should be clamped to prevent blood loss therefrom during perfusion of the spinal vasculature.

Alternatively, the spinal vasculature can be cooled with a medium other than oxygenated blood. For instance, a cooled biocompatible liquid, such as, e.g., saline solution can be flowed through the branched conduit 102 from an external source, such as, e.g., a intravenous bag (not shown).

A cylindrical region of the aorta 12 encompassing the aneurysm or dissection is then removed and the open ends of the aorta 12 are sutured to a graft. Inflation medium is removed from the inflation port 126 to deflate the balloon occluders 124, and the inflow cannula 108 and outflow cannulae 110 are respectively removed from the aorta 12 and individually severed intercostal arteries 14. The intercostal arteries 14 are then sutured to the graft, and the clamp 20 is removed from the aorta 12, restoring normal circulation to the spinal vasculature.

Figure 8:
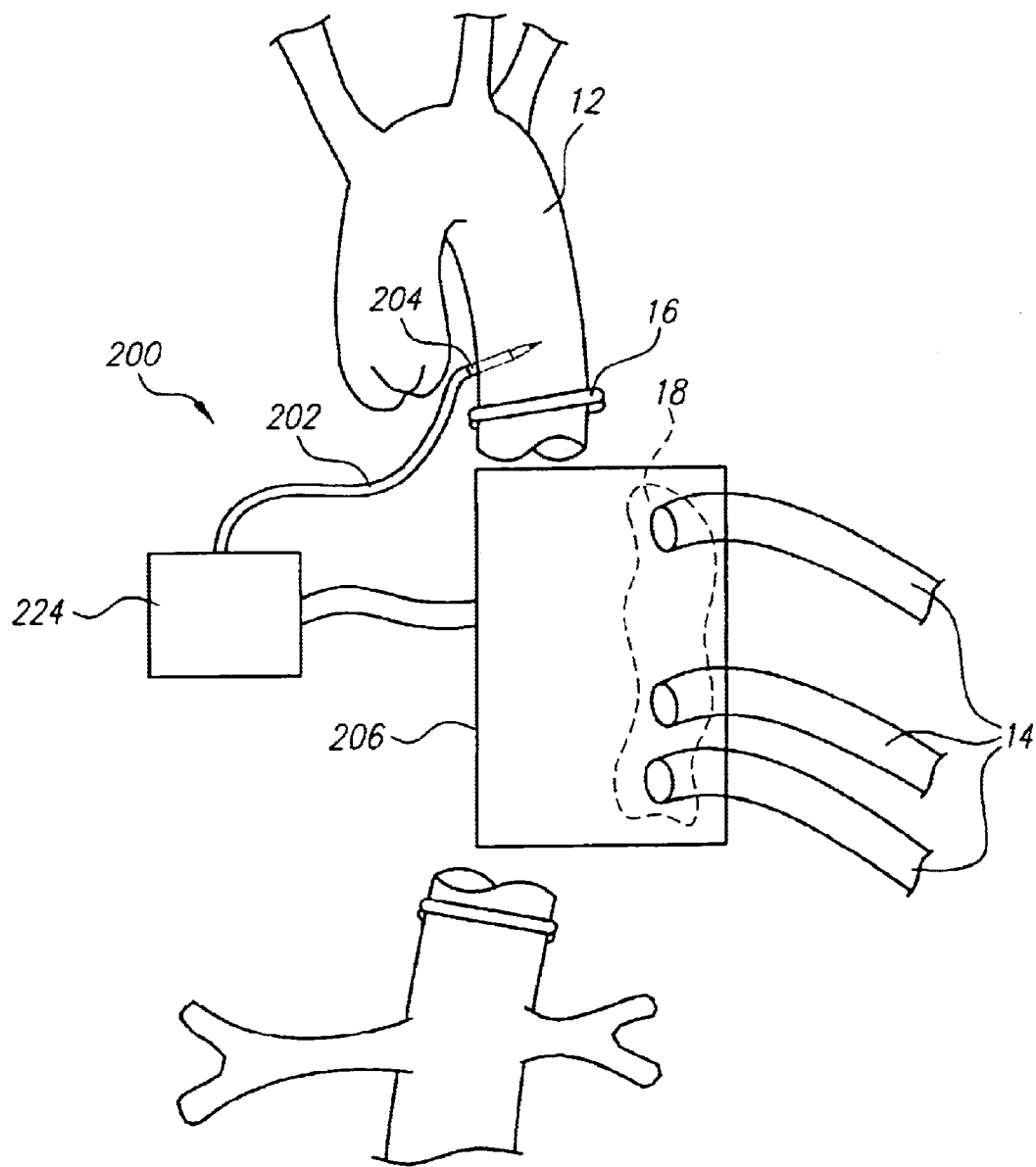
FIG. 8 illustrates a preferred method of simultaneously flowing oxygenated blood from the aorta into the open ends of a plurality of integrally severed intercostal arteries by employing the multiple vessel perfusion assembly of FIG. 4.

With reference to FIG. 8, selective spinal vasculature perfusion performed in accordance with a preferred method of the present invention is described in the context of another aortic grafting procedure. Instead of severing the intercostal arteries 14 individually from the aorta 12 as described above, however, an aortic patch 18 (shown in phantom) adjacent the damaged region is excised to integrally severe the intercostal arteries 14 from the aorta 12.

Figure 9:
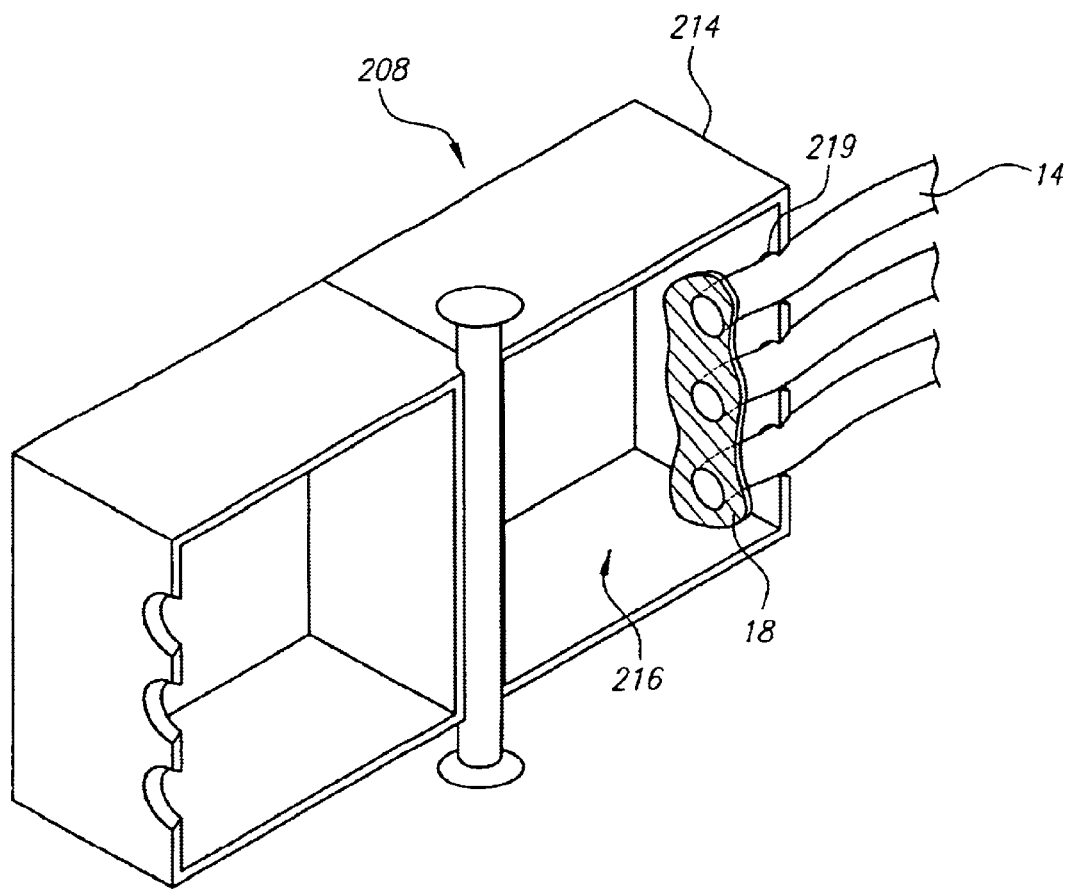
FIG. 9 illustrates a preferred method of placing the open ends of a plurality of integrally severed intercostal arteries within the perfusion chamber of FIG. 5.

Employment of the chambered multiple vessel perfusion assembly 100 described above can be particularly useful in perfusing such integrally severed intercostal arteries 14. In this connection, the inflow cannula 204 is inserted through the wall of the aorta 12, much like the inflow cannula 108 described above. The aortic patch 18 is placed within the substantially enclosed cavity 210 of the perfusion chamber 206 and the integrally severed intercostal arteries 14 are engaged within the vessel engaging outlets 212, with the openings of the integrally severed intercostal arteries 14 being in fluid communication with the substantially enclosed cavity 210. In particular, with the perfusion chamber 206 open as depicted in FIG. 9, the integrally severed intercostal arteries 14 are disposed within notches 219 of one of the opposing structures 214 with the aortic patch 18 lying within the open cavity 216 of the opposing structure 214. The perfusion chamber 206 is then closed to seal the open ends of the integrally severed intercostal arteries 14 within the perfusion chamber 206.

The control device 224 is operated in much the same manner as the control device 128 described above to control the perfusion of blood within the spinal vasculature. That is, the pump 226 controllingly flows oxygenated blood from the aorta 12 into the inflow cannula 204, through the conduit 202, into the perfusion chamber 206 and out through the lumens of the integrally severed intercostal arteries 14 to the spinal vasculature. The cooler 224 refrigerates the blood as it travels through the conduit 202, thereby inducing selective hypothermia within the spinal vasculature.

It should be noted that although the use of the multiple vessel perfusion assemblies 100 and 200 were respectively described with reference to individually severed intercostal arteries 14 and integrally severed intercostal arteries 14, the assemblies 100 and 200 are interchangeable in this respect. For instance, the branched multiple vessel perfusion assembly 100 can be employed to perfuse blood within intercostal arteries 14 that have been integrally severed from the aorta 12. Likewise, the chambered multiple vessel perfusion assembly 100 can be employed to perfuse blood within intercostal arteries 14 that have been individually severed from the aorta 12.

Figure 13:
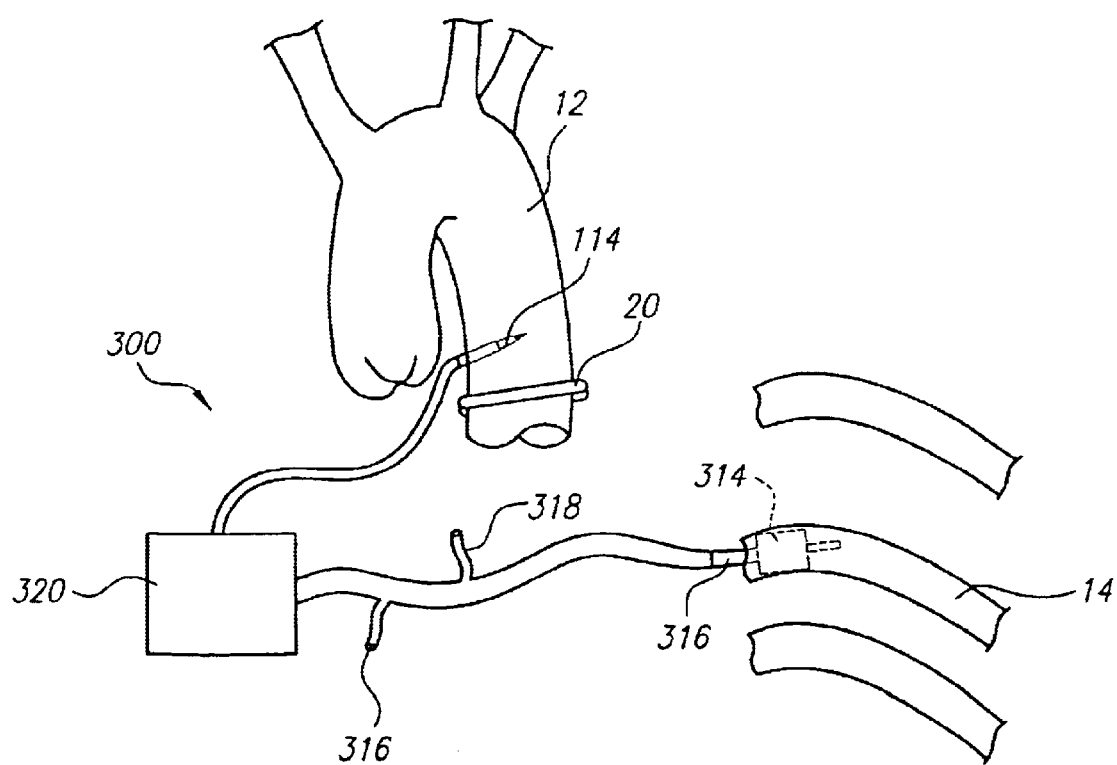
FIG. 13 illustrates an embodiment of a single vessel perfusion assembly for use in the perfusion of a single intercostal artery.

With reference to FIG. 13, employment of the single vessel perfusion assembly 300 described above can be particularly useful in perfusing a single intercostal artery 14. In this connection, the outflow cannula 306 (shown partially in phantom) is inserted within the open end of a severed intercostal artery 14, and the inflow cannula 304 (shown partially in phantom) is inserted through the wall of the aorta 12, much like the outflow cannulae 110 and inflow cannula 108 described above. Inflation medium is then conveyed through the inflation port 316 to inflate the balloon occluder 314, thereby sealing the blood flow outlet 312 within the intercostal artery 14. To further protect the spinal vasculature, a neuroprotective agent can be flowed into the drug delivery port 318.

The control device 320 is operated in much the same manner as the control device 128 described above to control the perfusion of blood within the spinal vasculature. That is, the pump 322 controllingly flows oxygenated blood from the aorta 12 into the inflow cannula 304, through the conduit 302, out the outflow cannula 306, and out through the lumen of the intercostal artery 14 to the spinal vasculature. The cooler 324 refrigerates the blood as it travels through the conduit 302, thereby inducing selective hypothermia within the spinal vasculature.

Figure 10:
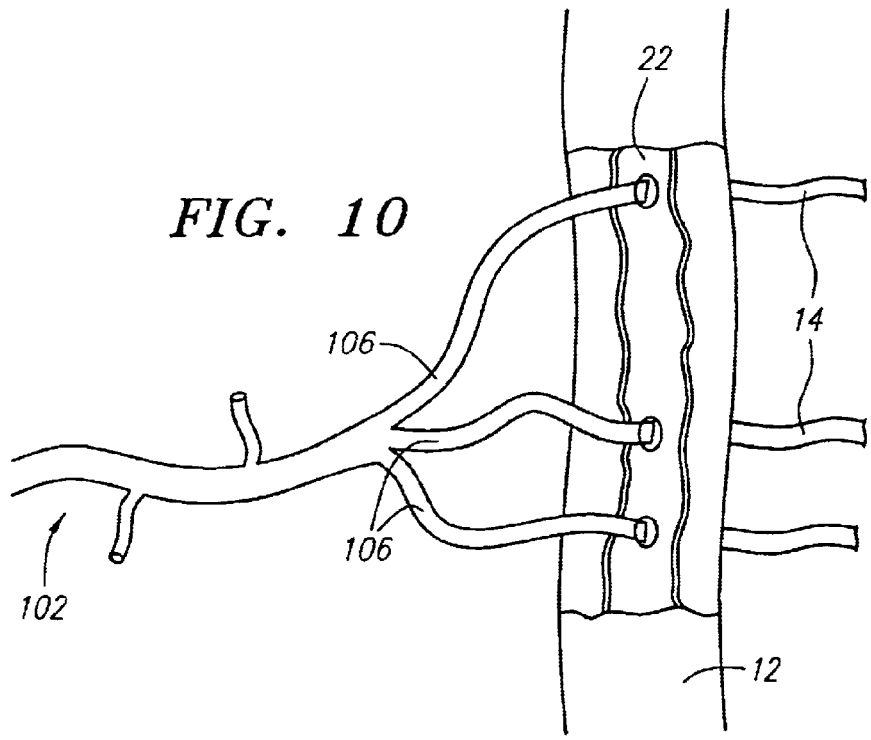
FIG. 10 illustrates a preferred method of simultaneously flowing oxygenated blood from the aorta into the open ends of a plurality of intercostal arteries through a slit in the aorta.
Figure 11:
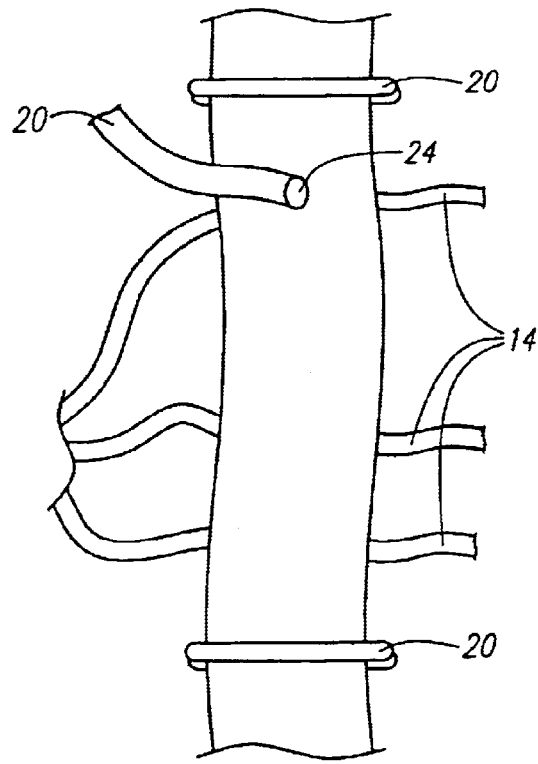
FIG. 11 illustrates a preferred method of simultaneously flowing oxygenated blood from the aorta into the open ends of a plurality of intercostal arteries through a puncture in the aorta.

It should also be noted that the methods of the present invention are not limited by the type of grafting surgery performed, but can be practiced whenever the open ends of intercostal arteries can be accessed. For instance, the open ends of unsevered intercostal arteries 14 can be accessed through a slit 22 made within the wall of the aorta (FIG. 10). Such a procedure finds its usefulness in grafting that involves removing a longitudinal section of the aorta 12 rather than a cylindrical section. In this case, the open ends of the unsevered intercostal arteries 14 can be directly perfused in much the same manner as that described above with respect to the branched multiple vessel perfusion assembly 100. The open ends of unsevered intercostal arteries 12 can also be accessed through a puncture 24 made within the wall of the aorta (FIG. 11). In this case, clamps 20 can be used to bracket the intercostal arteries 14 to be perfused, and a shunt 26 can be employed to flow a medium, such as oxygenated blood from the aorta 12, through the puncture 24 within the wall of the aorta 12, where the medium is dispersed among the bracketed intercostal arteries 14.

While preferred methods and embodiments have been shown and described, it will be apparent to one of ordinary skill in the art that numerous alterations may be made without departing from the spirit or scope of the invention. Therefore, the invention is not to be limited except in accordance with the following claims.

What is claimed is:

1. A vessel perfusion assembly, comprising:
   a tubular member having a first end adapted to enter a first vessel, a second end, and a lumen therebetween;
   a plurality of tubular branches attached to the second end of the tubular member, each tubular branch having a lumen communicating with the lumen of the tubular member and a distal opening adapted to enter a second vessel;
   a sealing mechanism disposed about the distal opening of each tubular branch;
   an extracorporeal cooler communicating with the lumen of the tubular member; and
   a thermostat for measuring the temperature of blood flowing through the lumen,
   wherein, during use, the first end of the tubular member is inserted into the first vessel, the distal end of each tubular branch is inserted into the second vessel and sealed, and blood flows from the first vessel through the lumen of the tubular member, and the blood is cooled before flowing into each second vessel through each lumen of each tubular branch.

2. The assembly of claim 1, wherein the sealing mechanism comprises a balloon occluder.

3. The assembly of claim 1, wherein the first end of the tubular member includes a sharpened tip for piercing a wall of a body cavity.

4. The assembly of claim 1, wherein the first end of the tubular member includes a blunt tube insertable through an incision in a wall of a body cavity.

5. The assembly of claim 1, wherein each second vessel is an intercostal artery.

6. The assembly of claim 1, further comprising a pump for controlling the flow of blood through the lumen.

7. The assembly of claim 1, wherein the cooler is disposed within the lumen of the tubular member.

8. The assembly of claim 1, wherein each tubular member comprises elastomeric tubing.

9. A method for cooling the spinal vasculature of a patient, comprising the steps of:
   providing a tubular member having a first end adapted to enter a first vessel, a second end, a lumen therebetween, a plurality of tubular branches attached to the second end of the tubular member, each tubular branch having a lumen communicating with the lumen of the tubular member and a distal opening adapted to enter a spinal or intercostal artery;
   inserting the first end of the tubular member into the first vessel;
   inserting the distal end of each tubular branch into the spinal or intercostal artery;
   sealing the distal end of each tubular branch;
   extracorporeally cooling the blood which flows from the first vessel through the lumen of the tubular member;
   flowing the cooled blood through each tubular branch into the spinal or intercostal arteries and into the spinal vasculature;
   accessing the aorta upstream from the least one severed intercostal artery;
   cooling oxygenated blood from the aorta; and
   flowing the cooled oxygenated blood through the at least one intercostal artery.

10. The method of claim 9, wherein the blood is oxygenated blood.

11. The method of claim 10, wherein the oxygenated blood is taken from the aorta of the patient.

12. The method of claim 9, wherein the flow of the cooled blood is controlled by a pump.

13. The method of claim 12, wherein the cooled blood is flowed at a rate of between 100 ml/minute to 1000 ml/minute.

14. The method of claim 7, further comprising the step of severing the spinal or intercostal artery.

15. The method of claim 9, wherein the distal end of each tubular branch is inserted directly into the open end of the spinal or intercostal artery.

16. The method of claim 9, wherein the distal end of each tubular branch is inserted into the open end of the spinal or intercostal artery through a slit in the aorta.

17. The method of claim 9, wherein the distal end of each tubular branch is inserted into the open end of the spinal or intercostal artery through a puncture in the wall of the aorta.

18. The method of claim 9, wherein the blood flows simultaneously into a plurality of intercostal arteries.

19. The method of claim 9, wherein hypothermia is localized in the spinal vasculature, while keeping the rest of the body normothermic.

20. The method of claim 9, wherein the oxygenated blood is cooled to between 4° C. and 35° C.

21. The method of claim 9, wherein each tubular branch further comprises a balloon occluder disposed about the distal opening.

22. A vessel perfusion assembly, comprising:

a tubular member having a first end adapted to enter a first vessel, a second end, and a lumen therebetween;

a plurality of tubular branches attached to the second end of the tubular member, each tubular branch having a lumen communicating with the lumen of the tubular member and a distal opening adapted to enter a second vessel;

a sealing mechanism disposed about the distal opening of each tubular branch; and an extracorporeal cooler communicating with the lumen of the tubular member, wherein, during use, the first end of the tubular member is inserted into the first vessel, the distal end of each tubular branch is inserted into the second vessel and sealed, and blood flows from the first vessel through the lumen of the tubular member, and the blood is cooled before flowing into each second vessel through each lumen of each tubular branch, and wherein each tubular branch comprises a manometer for measuring blood pressure within each second vessel.

23. The assembly of claim 22, wherein the sealing mechanism comprises a balloon occluder.

24. The assembly of claim 22, wherein the first end of the tubular member includes a sharpened tip for piercing a wall of a body cavity.

25. The assembly of claim 22, wherein the first end of the tubular member includes a blunt tube insertable through an incision in a wall of a body cavity.

26. The assembly of claim 22, wherein each second vessel is an intercostal artery.

27. The assembly of claim 22, further comprising a pump for controlling the flow of blood through the lumen.

28. The assembly of claim 22, wherein the cooler is disposed within the lumen of the tubular member.

29. The assembly of claim 22, wherein each tubular member comprises elastomeric tubing.

* * * * *